US010980663B2

(12) United States Patent
Eskaros et al.

(10) Patent No.: US 10,980,663 B2
(45) Date of Patent: Apr. 20, 2021

(54) MEDICAL DEVICE FOR USE WITH A STOMA

(71) Applicant: W. L. Gore & Associates, Inc., Newark, DE (US)

(72) Inventors: Sherif A. Eskaros, Elkton, MD (US); David C. Everson, Elkton, MD (US); George N. Foutrakis, Oxford, PA (US); John M. Herman, Elkton, MD (US); Matthew A. Johnson, Bear, DE (US); Peter J. Lutz, Elkton, MD (US); Michael L. O'Hara, Havre de Grace, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 397 days.

(21) Appl. No.: 15/947,059

(22) Filed: Apr. 6, 2018

(65) Prior Publication Data

US 2018/0221194 A1    Aug. 9, 2018

Related U.S. Application Data

(63) Continuation of application No. 13/413,921, filed on Mar. 7, 2012, now Pat. No. 10,864,106.
(Continued)

(51) Int. Cl.
*A61F 2/04* (2013.01)
*A61F 5/445* (2006.01)
(Continued)

(52) U.S. Cl.
CPC ......... *A61F 5/445* (2013.01); *A61M 39/0247* (2013.01); *A61F 2/064* (2013.01); *A61F 2/07* (2013.01); *A61F 2005/4455* (2013.01)

(58) Field of Classification Search
CPC ...... A61F 2/04; A61F 2/06; A61F 2/07; A61F 2/82; A61F 2/84; A61F 5/44
See application file for complete search history.

(56) References Cited

U.S. PATENT DOCUMENTS 3,818,511 A    6/1974  Goldberg
4,119,100 A    10/1978 Rickett
(Continued)

FOREIGN PATENT DOCUMENTS

CN    101951983 A    1/2011
EP    0991375 B1    9/2004
(Continued)

OTHER PUBLICATIONS

International Search Report and Written Opinion from PCT/US2012/027984, dated Jun. 6, 2012, 11 pages.
(Continued)

*Primary Examiner* — Tatyana Zalukaeva
*Assistant Examiner* — Ilya Y Treyger (57) ABSTRACT

An device including a proximal portion adapted for placement intermediately within a hollow body cavity to capture and divert contents; the proximal portion being expandable from an initial state with an initial diameter, into an expanded state with a diameter greater than the initial diameter for engaging the proximal portion with an inner wall of the hollow body cavity; and a distal portion, connected to the proximal portion, adapted to extend through the abdominal wall or into the intestine to conduct the hollow body cavity contents out of the proximal portion.

21 Claims, 12 Drawing Sheets

Related U.S. Application Data (60) Provisional application No. 61/450,422, filed on Mar. 8, 2011.

(51) Int. Cl.
  *A61M 39/02* (2006.01)
  *A61F 2/06* (2013.01)
  *A61F 2/07* (2013.01)
  *A61F 2/82* (2013.01)
  *A61F 5/44* (2006.01)

(56) References Cited

U.S. PATENT DOCUMENTS

| | | | |
|---|---|---|---|
| 4,338,937 A | 7/1982 | Lerman | |
| 4,381,765 A | 5/1983 | Burton | |
| 5,224,953 A | 7/1993 | Morgentaler | |
| 5,261,898 A | 11/1993 | Polin | |
| 5,354,308 A | 10/1994 | Simon et al. | |
| 5,562,728 A | 10/1996 | Lazarus et al. | |
| 5,741,297 A | 4/1998 | Simon | |
| 5,755,778 A | 5/1998 | Kleshinski | |
| 5,797,933 A | 8/1998 | Snow | |
| 5,830,222 A | 11/1998 | Makower | |
| 5,868,783 A | 2/1999 | Tower | |
| 5,945,994 A | 8/1999 | Shimizu et al. | |
| 5,957,949 A | 9/1999 | Leonhardt | |
| 6,007,544 A | 12/1999 | Kim | |
| 6,077,291 A | 6/2000 | Das | |
| 6,165,209 A * | 12/2000 | Patterson | A61F 2/90 606/159 |
| 6,168,621 B1 | 1/2001 | Vrba | |
| 6,171,329 B1 | 1/2001 | Shaw et al. | |
| 6,193,734 B1 | 2/2001 | Bolduc | |
| 6,214,029 B1 | 4/2001 | Thill et al. | |
| 6,217,608 B1 | 4/2001 | Penn et al. | |
| 6,290,728 B1 | 9/2001 | Phelps | |
| 6,315,708 B1 | 11/2001 | Salmon et al. | |
| 6,315,792 B1 | 11/2001 | Armstrong et al. | |
| 6,355,052 B1 | 3/2002 | Neuss et al. | |
| 6,391,036 B1 | 5/2002 | Berg et al. | |
| 6,391,039 B1 | 5/2002 | Nicholas et al. | |
| 6,416,543 B1 | 7/2002 | Hilaire et al. | |
| 6,419,681 B1 | 7/2002 | Vargas | |
| 6,432,127 B1 | 8/2002 | Kim et al. | |
| 6,485,496 B1 | 11/2002 | Suyker et al. | |
| 6,485,507 B1 | 11/2002 | Walak et al. | |
| 6,488,702 B1 | 12/2002 | Besselink | |
| 6,579,314 B1 | 6/2003 | Lombardi et al. | |
| 6,585,758 B1 | 7/2003 | Chouinard et al. | |
| 6,616,675 B1 | 9/2003 | Evard et al. | |
| 6,629,992 B2 | 10/2003 | Bigus et al. | |
| 6,666,883 B1 | 12/2003 | Seguin et al. | |
| 6,712,836 B1 | 3/2004 | Berg et al. | |
| 6,863,684 B2 | 3/2005 | Kim et al. | |
| 6,866,674 B2 | 3/2005 | Galdonik | |
| 6,911,037 B2 | 6/2005 | Gainor et al. | |
| 6,945,994 B2 | 9/2005 | Austin et al. | |
| 6,958,037 B2 | 10/2005 | Ewers | |
| 7,022,131 B1 | 4/2006 | Derowe et al. | |
| 7,025,777 B2 | 4/2006 | Moore | |
| 7,029,482 B1 | 4/2006 | Vargas et al. | |
| 7,037,344 B2 | 5/2006 | Kagan | |
| 7,115,136 B2 | 10/2006 | Park | |
| 7,182,771 B1 | 2/2007 | Houser | |
| 7,223,274 B2 | 5/2007 | Vargas | |
| 7,252,680 B2 | 8/2007 | Freitag | |
| 7,303,569 B2 | 12/2007 | Yencho et al. | |
| 7,431,729 B2 | 10/2008 | Chanduszko | |
| 7,585,306 B2 | 9/2009 | Abbott | |
| 7,608,086 B2 | 10/2009 | Tanaka et al. | |
| 7,632,302 B2 | 12/2009 | Vreeman et al. | |
| 7,780,686 B2 | 8/2010 | Park | |
| 7,828,814 B2 | 11/2010 | Brenneman et al. | |
| 7,892,247 B2 | 2/2011 | Conston et al. | |
| 7,901,430 B2 | 3/2011 | Matsuura | |
| 8,043,360 B2 | 10/2011 | McNamara et al. | |
| 8,109,946 B2 | 2/2012 | Cahill | |
| 8,114,125 B2 | 2/2012 | Seibold et al. | |
| 8,197,498 B2 | 6/2012 | Coleman | |
| 8,257,389 B2 | 9/2012 | Chanduszko et al. | |
| 8,262,691 B2 | 9/2012 | McGuckin | |
| 8,343,088 B2 | 1/2013 | Bates | |
| 8,398,676 B2 | 3/2013 | Roorda et al. | |
| 8,425,539 B2 | 4/2013 | Binmoeller | |
| 8,430,934 B2 | 4/2013 | Das | |
| 8,435,284 B2 | 5/2013 | Eidenschink | |
| 8,454,632 B2 | 6/2013 | Binmoeller et al. | |
| 8,579,935 B2 | 11/2013 | Devries et al. | |
| 8,641,747 B2 | 2/2014 | Brenneman et al. | |
| 8,679,171 B2 | 3/2014 | Deem et al. | |
| 8,728,155 B2 | 5/2014 | Montorfano | |
| 8,740,940 B2 | 6/2014 | Maahs | |
| 8,864,813 B2 | 10/2014 | Barr | |
| 8,870,916 B2 | 10/2014 | Ewers | |
| 8,992,604 B2 | 3/2015 | Gross et al. | |
| 9,597,204 B2 | 3/2017 | Benary | |
| 9,668,853 B2 | 6/2017 | Shin | |
| 9,782,533 B2 | 10/2017 | Brenneman et al. | |
| 9,993,251 B2 | 6/2018 | Todd et al. | |
| 10,004,509 B2 | 6/2018 | Todd | |
| 10,363,040 B2 | 7/2019 | Sambandam | |
| 2001/0021872 A1 | 9/2001 | Bailey et al. | |
| 2002/0082627 A1 | 6/2002 | Berg et al. | |
| 2002/0099431 A1 | 7/2002 | Armstrong et al. | |
| 2002/0099437 A1 | 7/2002 | Anson et al. | |
| 2002/0161341 A1 | 10/2002 | Stinson et al. | |
| 2002/0169475 A1 | 11/2002 | Gainor et al. | |
| 2002/0183787 A1 | 12/2002 | Wahr et al. | |
| 2003/0028213 A1 | 2/2003 | Thill et al. | |
| 2003/0032967 A1 | 2/2003 | Park | |
| 2003/0055441 A1 | 3/2003 | Suyker et al. | |
| 2003/0069533 A1 | 4/2003 | Kakutani et al. | |
| 2003/0139819 A1 | 7/2003 | Beer | |
| 2003/0191482 A1 | 10/2003 | Suyker et al. | |
| 2004/0073242 A1 | 4/2004 | Chanduszko | |
| 2004/0092977 A1 | 5/2004 | Vargas et al. | |
| 2004/0098105 A1 | 5/2004 | Stinson et al. | |
| 2004/0133236 A1 | 7/2004 | Chanduszko | |
| 2004/0211433 A1 | 10/2004 | Albright | |
| 2005/0049675 A1 | 3/2005 | Wallace | |
| 2005/0070934 A1 | 3/2005 | Tanaka | |
| 2005/0070935 A1 | 3/2005 | Ortiz | |
| 2005/0070957 A1 | 3/2005 | Das | |
| 2005/0154465 A1 | 7/2005 | Hodges | |
| 2005/0228413 A1 | 10/2005 | Binmoeller et al. | |
| 2005/0234509 A1 | 10/2005 | Widomski et al. | |
| 2005/0251201 A1 | 11/2005 | Roue et al. | |
| 2005/0273124 A1 | 12/2005 | Chanduszko | |
| 2005/0288786 A1 | 12/2005 | Chanduszko | |
| 2006/0047337 A1 | 3/2006 | Brenneman | |
| 2006/0052821 A1 | 3/2006 | Abbott et al. | |
| 2006/0106418 A1 | 5/2006 | Seibold et al. | |
| 2006/0217761 A1 | 9/2006 | Opolski | |
| 2007/0055358 A1 | 3/2007 | Krolik et al. | |
| 2007/0073337 A1 | 3/2007 | Abbott et al. | |
| 2007/0123917 A1 | 5/2007 | Ortiz et al. | |
| 2007/0244518 A1 | 10/2007 | Callaghan | |
| 2007/0249985 A1 | 10/2007 | Brenneman et al. | |
| 2007/0282430 A1 | 12/2007 | Thommen et al. | |
| 2007/0283552 A1 | 12/2007 | Gale | |
| 2008/0086168 A1 | 4/2008 | Cahill | |
| 2008/0091235 A1 | 4/2008 | Sirota | |
| 2008/0243151 A1 | 10/2008 | Binmoeller et al. | |
| 2008/0262518 A1 | 10/2008 | Freudenthal | |
| 2009/0076541 A1 | 3/2009 | Chin et al. | |
| 2009/0090366 A1 | 4/2009 | Cuevas | |
| 2009/0143713 A1 | 6/2009 | Van et al. | |
| 2009/0228038 A1 | 9/2009 | Amin | |
| 2009/0281557 A1 | 11/2009 | Sander et al. | |
| 2010/0010520 A1 | 1/2010 | Takahashi et al. | |
| 2010/0023132 A1 | 1/2010 | Imran | |
| 2010/0100105 A1 | 4/2010 | Bates | |
| 2010/0106171 A1 | 4/2010 | Arepally et al. | |

(56) References Cited

U.S. PATENT DOCUMENTS

| | | |
|---|---|---|
| 2010/0114128 A1 | 5/2010 | Coleman |
| 2010/0114290 A1 | 5/2010 | Rasmussen et al. |
| 2010/0130995 A1 | 5/2010 | Yevzlin et al. |
| 2010/0174253 A1 | 7/2010 | Cline et al. |
| 2010/0234878 A1 | 9/2010 | Hruska et al. |
| 2010/0268316 A1 | 10/2010 | Brenneman et al. |
| 2010/0305590 A1 | 12/2010 | Holmes et al. |
| 2011/0040366 A1 | 2/2011 | Goetz |
| 2011/0054381 A1 | 3/2011 | Van et al. |
| 2011/0118765 A1 | 5/2011 | Aguirre |
| 2011/0213415 A1 | 9/2011 | McGuckin, Jr. |
| 2011/0218609 A1 | 9/2011 | Chobotov et al. |
| 2011/0257461 A1 | 10/2011 | Lipperman et al. |
| 2011/0257723 A1 | 10/2011 | McNamara |
| 2012/0065652 A1 | 3/2012 | Cully et al. |
| 2012/0089216 A1 | 4/2012 | Rapaport et al. |
| 2012/0130417 A1 | 5/2012 | Lepulu et al. |
| 2012/0172927 A1 | 7/2012 | Campbell et al. |
| 2012/0232505 A1 | 9/2012 | Eskaros |
| 2013/0012969 A1 | 1/2013 | Shin |
| 2013/0030521 A1 | 1/2013 | Nitzan et al. |
| 2013/0041451 A1 | 2/2013 | Patterson et al. |
| 2013/0053784 A1 | 2/2013 | Houser et al. |
| 2013/0165967 A1 | 6/2013 | Amin |
| 2013/0218192 A1 | 8/2013 | Erzberger et al. |
| 2013/0245742 A1 | 9/2013 | Norris |
| 2013/0261531 A1 | 10/2013 | Gallagher et al. |
| 2013/0317546 A1 | 11/2013 | Brown |
| 2014/0012368 A1 | 1/2014 | Sugimoto et al. |
| 2014/0031842 A1 | 1/2014 | Brenneman et al. |
| 2014/0074155 A1 | 3/2014 | Rothstein et al. |
| 2014/0236064 A1 | 8/2014 | Binmoeller et al. |
| 2014/0343602 A1 | 11/2014 | Cox et al. |
| 2015/0005810 A1 | 1/2015 | Center et al. |
| 2015/0066077 A1 | 3/2015 | Akpinar |
| 2015/0313595 A1 | 11/2015 | Houghton et al. |
| 2015/0313599 A1 | 11/2015 | Johnson et al. |
| 2016/0135813 A1 | 5/2016 | Johnson et al. |
| 2016/0256169 A1 | 9/2016 | Ben-Muvhar et al. |
| 2017/0020498 A1 | 1/2017 | Blom |
| 2018/0242972 A1 | 8/2018 | Todd |
| 2018/0250009 A1 | 9/2018 | Todd et al. |
| 2018/0296809 A1 | 10/2018 | Johnson |

FOREIGN PATENT DOCUMENTS

| | | |
|---|---|---|
| EP | 1790297 | 5/2007 |
| EP | 1480565 B1 | 12/2008 |
| EP | 2543323 A1 | 1/2013 |
| GB | 2409978 A | 7/2005 |
| JP | 2001-520908 A | 11/2001 |
| JP | 2001340346 | 12/2001 |
| JP | 2005518863 | 6/2005 |
| JP | 2005-528181 A | 9/2005 |
| JP | 2005-534390 A | 11/2005 |
| JP | 2006-006648 A | 1/2006 |
| JP | 2007530128 A | 11/2007 |
| JP | 2009-518149 A | 5/2009 |
| JP | 2010528821 A | 8/2010 |
| JP | 2011-519709 A | 7/2011 |
| JP | 2013-013715 A | 1/2013 |
| WO | WO-1997027898 A1 | 8/1997 |
| WO | 97/32543 A1 | 9/1997 |
| WO | 98/02099 A1 | 1/1998 |
| WO | 98/08462 A2 | 3/1998 |
| WO | WO-1998016174 A1 | 4/1998 |
| WO | 98/58600 A1 | 12/1998 |
| WO | 01/72367 A1 | 10/2001 |
| WO | WO-2003073944 A1 | 9/2003 |
| WO | 2003/103476 A2 | 12/2003 |
| WO | 2004/012603 A2 | 2/2004 |
| WO | 2004/087236 A2 | 10/2004 |
| WO | WO-2005089655 | 9/2005 |
| WO | 2007/024964 A1 | 3/2007 |
| WO | 2007/053243 A2 | 5/2007 |
| WO | 2007/100970 A2 | 9/2007 |
| WO | WO-2008157172 A1 | 12/2008 |
| WO | WO-2009109348 A1 | 9/2009 |
| WO | WO-2009140195 A1 | 11/2009 |
| WO | 2009/146369 A1 | 12/2009 |
| WO | WO-2010129162 | 11/2010 |
| WO | 2012/034108 A1 | 3/2012 |
| WO | 2012/071075 A1 | 5/2012 |
| WO | WO-2012067912 A1 | 5/2012 |
| WO | 2013/152891 A2 | 10/2013 |
| WO | 2015/168501 A2 | 11/2015 |
| WO | 2015/168504 A2 | 11/2015 |
| WO | 2015/168506 A1 | 11/2015 |

OTHER PUBLICATIONS

International Search Report from PCT/US2015/028717, dated Aug. 26, 13 pages.
European Search Report and Search Opinion Received for EP Application No. 15196870.8, dated May 17, 2016, 7 pages.
Extended European Search Report from EP18161679.8, dated Jun. 20, 2018, 7 pages.
International Preliminary Report on Patentability received for PCT Patent Application No. PCT/US15/28711, dated Nov. 17, 2016, 11 pages.
International Preliminary Report on Patentability received for PCT Patent Application No. PCT/US15/28715, dated Nov. 17, 2016, 8 pages.
International Preliminary Report on Patentability received for PCT Patent Application No. PCT/US15/28717, dated Nov. 17, 2016, 9 pages.
International Preliminary Report on Patentability received for PCT Patent Application No. PCT/US15/28721, dated Nov. 17, 2016, 8 pages.
International Preliminary Report on Patentability received for PCT Patent Application No. PCT/US2012/027984, dated Sep. 19, 2013, 8 pages.
International Search Report and Written Opinion from PCT/US2015/028707, dated Oct. 23, 2015, 19 pages.
International Search Report and Written Opinion from PCT/US2015/028721, dated Oct. 28, 2015, 13 pages.
International Search Report and Written Opinion from PCT/US2018/028120, dated Aug. 21, 2018, 17 pages.
International Search Report and Written Opinion received for PCT Patent Application No. PCT/US15/28711, dated Feb. 1, 2016, 17 pages.
International Search Report and Written Opinion received for PCT Patent Application No. PCT/US15/28715, dated Aug. 25, 2015, 12 pages.
International Search Report and Written Opinion received for PCT Patent Application No. PCT/US15/28717, dated Aug. 26, 2015, 13 pages.
International Search Report for PCT/US2016/055255 dated Dec. 20, 2016 and dated Jan. 20, 2017, 5 pages.

\* cited by examiner

MEDICAL DEVICE FOR USE WITH A STOMA

CROSS REFERENCE TO RELATED APPLICATION

This application is a continuation of U.S. application Ser. No. 13/413,921, filed Mar. 7, 2012, which claims priority to provisional application Ser. No. 61/450,422, filed Mar. 8, 2011, which are incorporated herein by reference in their entireties for all purposes.

FIELD OF INVENTION

This invention relates to a device for use in percutaneous applications by patients who have undergone surgery as a result of which an opening or stoma has been left in the wall of a hollow body cavity, such as an intestine, and/or in the abdominal wall.

BACKGROUND OF THE INVENTION

For patients having intestinal surgery or other operations to repair or remove a section of intestine, it is frequently necessary to perform a colostomy operation or an ileostomy operation. With a colostomy, the large intestine is brought through the abdominal wall, and with an ileostomy, the small intestine is brought through the abdominal wall. In each case, an opening called a stoma is created to provide a conduit for allowing elimination of waste material from the patient's body. Drainage or discharge from the digestive system of the patient takes place through the opening or stoma in the abdominal wall. The body duct protruding from the abdominal wall is typically sutured or otherwise adhered to the skin surrounding the opening. A flexible bag or other receiving means is typically attached to the stoma to collect and retain liquid, solid, and gaseous waste material eliminated through the stoma.

Figure 1A:
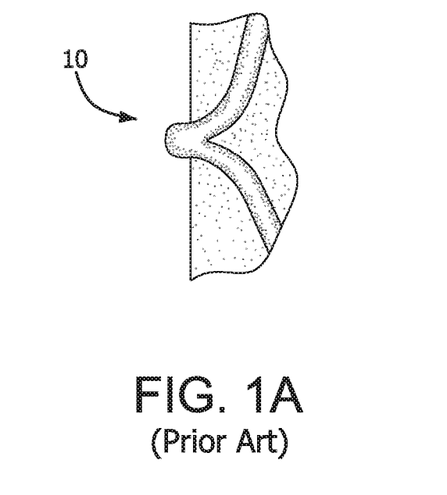
FIG. 1A is a side view of a loop ileostomy according to the prior art.
Figure 1B:
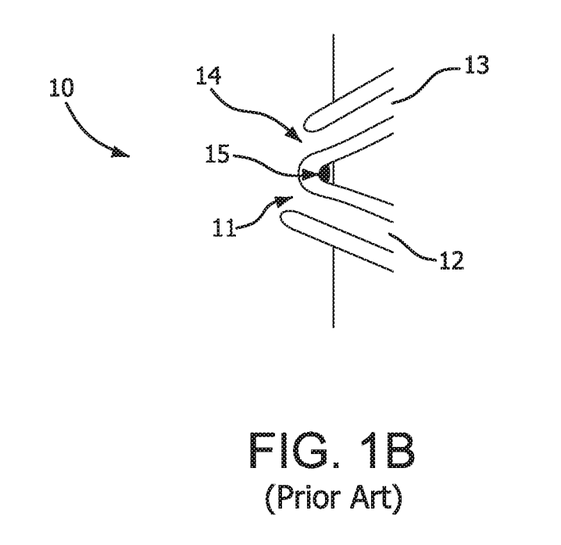
FIG. 1B is a schematic side view of a loop ileosotmy according to the prior art.

An exemplary such procedure is illustrated in FIGS. 1A and 1B, showing a loop ileostomy 10. The stoma 14 is created by cutting the loop of the intestine protruding from the abdomen. Upstream section 13 of the intestine empties the intestinal contents through the stoma. A mucous fistula 11 is formed on the downstream end 12 of the intestine, typically blocking that section from receiving intestinal contents while the stoma is in place. A shunt 15 is sometimes used between the skin and the loop of intestine.

Externalizing the intestine to form a stoma has disadvantages. It is sometimes difficult to control the flow of intestinal contents and there arises a consequential risk of infection and skin irritation. Attachment of ostomy appliances for collection of the intestinal matter can also be difficult. Stenosis and prolapse of the intestine are additional risks with this type of procedure.

A similar procedure might be undertaken to connect two hollow body cavities or organs within the body, thereby allowing one organ to drain into another. For instance, a stoma, may be created in a hollow body cavity within the body in order to allow the cavity to drain into the GI tract.

SUMMARY OF THE INVENTION

Applicant has addressed the many disadvantages associated with conventional stomas by providing a device that can be utilized with a stoma and, for example, eliminates the need to externalize an intestine through the abdominal wall. In an exemplary embodiment, the invention provides a device including a proximal portion adapted for placement intermediately within an intestine, or other hollow body cavity or organ, to capture and divert contents; the proximal portion being expandable, optionally by using a self-expandable nitinol stent, from an initial state with an initial diameter smaller than a diameter of the intestine for insertion of the proximal portion into the intestine, for example, into an expanded state with a diameter greater than the initial diameter for engaging the proximal portion with an inner wall of the intestine; and a distal portion, connected to the proximal portion, adapted to extend through the abdominal wall, or alternatively into another hollow body cavity or organ, to conduct the contents out of the proximal portion. In an alternative embodiment, the device also includes a valve connected to the distal portion to provide continence, allowing contents to be selectively discharged from the distal portion. The device optionally includes a transitional portion connecting the proximal portion to the distal portion. The proximal portion is optionally compressible from the expanded state for removal of the proximal portion from the intestine or other hollow body cavity or organ.

In alternative embodiments, the distal portion has an adjustable length, either through compression, or by removing portions of the device in a controlled manner. The distal portion is also optionally corrugated. The device may be flexible, crush resistant, and kink resistant.

In another aspect, a method of draining hollow body cavity contents is provided comprising the steps of (a) making an incision in the GI tract; (b) making an incision into the hollow body cavity wall; (c) inserting through said incisions a device according to the present invention; (d) positioning said proximal portion within the hollow body cavity; (e) deploying said proximal portion to capture and divert hollow body cavity contents; and (f) positioning said distal portion within the GI tract to drain the hollow body cavity contents out of the proximal portion and into the GI tract.

In yet another aspect, the invention provides a method of diverting intestinal contents from an intestine without bringing the intestine through an abdomen comprising the steps of (a) making an incision through the abdominal wall; (b) making an incision into the intestine without severing an entire diameter of the intestine; (c) percutaneously inserting through the incisions a device of the present invention; (d) positioning the proximal portion within the intestine; (e) deploying the proximal portion to capture and divert intestinal contents; and (f) positioning the distal portion to extend through the abdominal wall to conduct the intestinal contents out of the proximal portion. Optionally, the invention includes the step of attaching a valve to the device to provide continence allowing intestinal contents to be selectively discharged from the device. Further optional steps include attaching the intestine to an inner wall of the abdomen to seal the intestine, and adjusting the length of the distal portion to account for the thickness of the abdominal wall. The invention also alternatively includes the step of removing said device from the intestine.

DETAILED DESCRIPTION OF THE INVENTION

Figure 2:
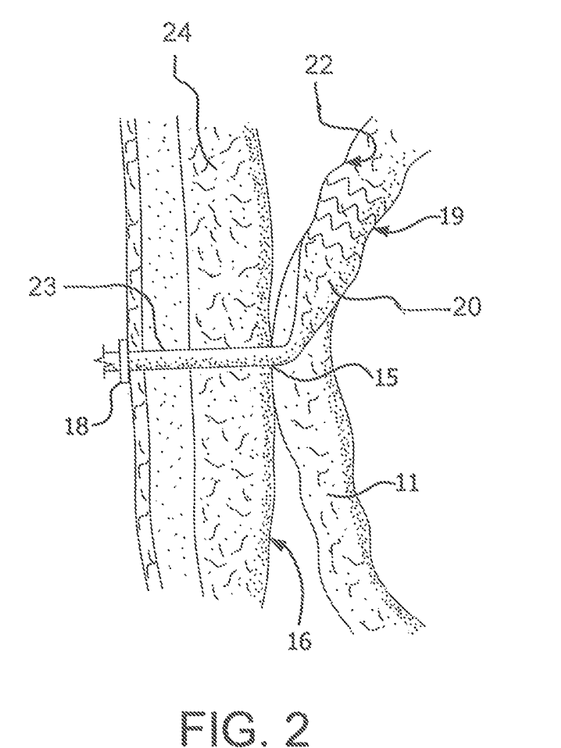
FIG. 2 is a side view of an exemplary embodiment of the present invention.

FIG. 2 illustrates an exemplary embodiment of a device according to the present invention. A proximal portion 20 of the device is disposed intermediately within an intestine 11. "Intermediately" as used herein means within the length of the intestine, as opposed to at a surgically severed end thereof. Proximal portion 20 is adapted to capture and divert intestinal contents from within intestine 11. The material of construction for proximal portion 20 may be durable biocompatible barrier material that prevents leaks and allows intestinal contents to pass along the internal length of proximal portion 20 without sticking to it. These attributes may be achieved by the material itself, or by combining the material with a suitable coating. Preferably, proximal portion 20 is made of a multilayer construction of fluoropolymer, such as expanded polytetrafluoroethylene (ePTFE). Alternative materials for proximal portion 20 include other fluoropolymers (such as FEP), polyethylene, polypropylene, polyolefins, polyimides, polyesters, silicone, fluorosilicone, and bioabsorbable materials such as polymers and copolymers of PGA, TMC, PLA and any combination of any of these materials. In certain embodiments, the barrier material of the proximal portion may comprise at least one aperture therein.

Proximal portion 20 includes support structure 19. Support structure 19 is preferably a self-expanding material, such as nitinol. Alternatively, support structure 19 is stainless steel or other biocompatible metal or polymer which is expandable by the application of an external force, such as balloon-expandable materials. Also alternatively, support structure 19 may be formed of a polymeric material. Support structure 19 may be bioabsorbable or nonbioabsorbable.

Support structure 19 may be disposed on the inside or the outside of the perimeter of proximal portion 20; that is, support structure 19 may be around the outside of the ePTFE (for example) used for the proximal portion 20, or it may be disposed inside the ePTFE used for proximal portion 20. It could alternatively be sandwiched between layers or coatings of the material used for proximal portion 20. In any case, it is attached to the ePTFE (for example) and is used to exert an outward force that engages the inner wall of intestine 11 and secures proximal portion 20 in place therein, allowing intestinal contents to be substantially fully diverted from intestine 11.

Support structure 19 enables proximal portion 20 to be expandable, from an initial state with an initial diameter smaller than the diameter of intestine 11 for insertion of the proximal portion into intestine 11, into an expanded state with a diameter greater than the initial diameter, for engaging the proximal portion 20 with an inner wall 22 of intestine 11. Proximal portion 20 is also compressible from its expanded state for removal of the proximal portion from the intestine 11.

Figure 3:
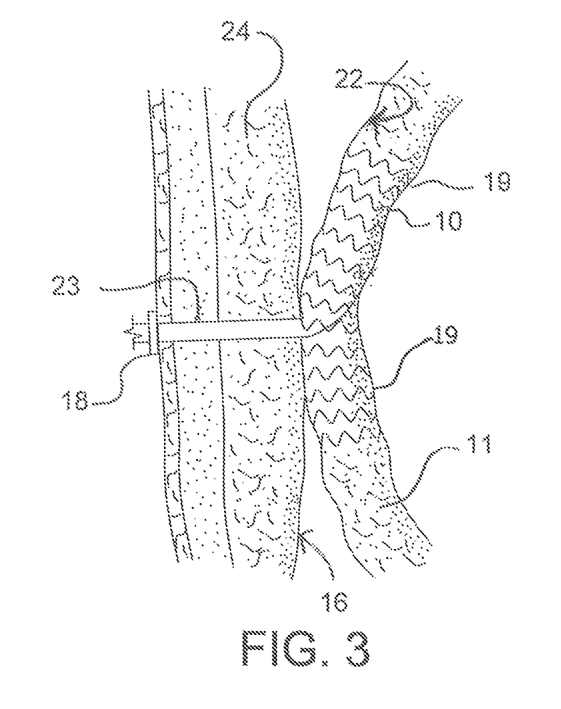
FIG. 3 is a side view of another exemplary embodiment of the present invention.

FIG. 3 illustrates an alternative embodiment of the present invention. Specifically, in FIG. 3, support structure 19 extends the length of proximal portion 20 and beyond, extending into intestine 11 below proximal portion 20. This structure provides for added reinforcement, and therefore patency, of intestine 11 at the stoma site. It limits twisting or kinking of intestine 11 near the stoma site, providing the benefit of preventing narrowing (such as by occlusion or obstruction) of intestine 11 leading to an undesirable slowdown of intestinal flow.

Figure 4:
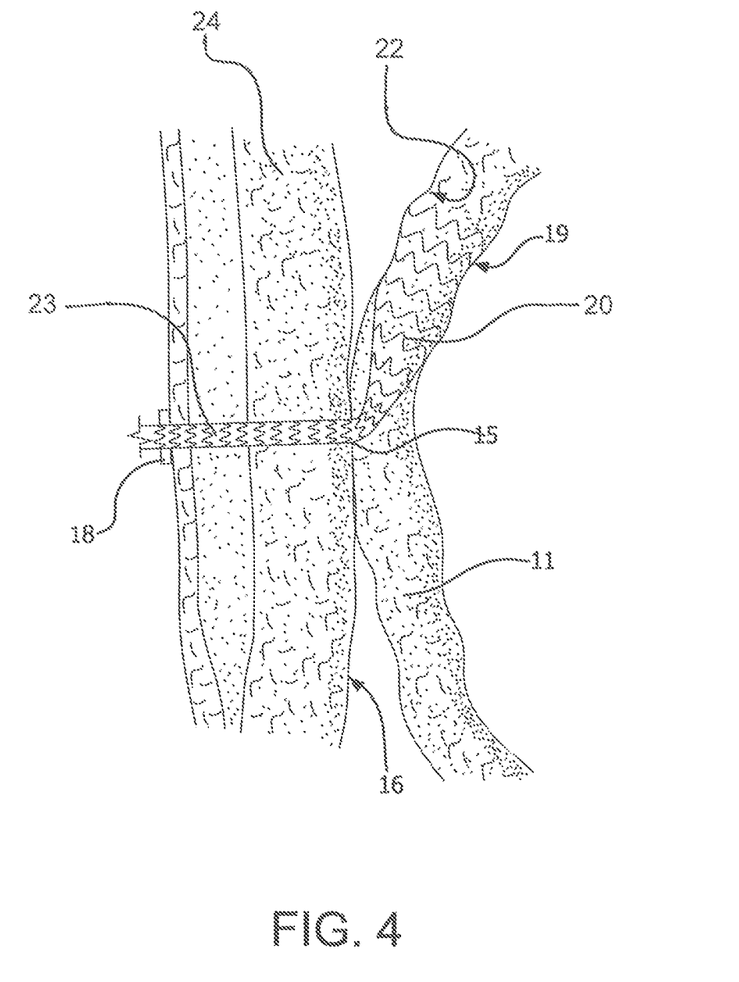
FIG. 4 is a side view of another exemplary embodiment of the present invention.

FIG. 4 illustrates an embodiment of the invention in which support structure 19 is included in distal portion 23. The support structure can be of the same alternative constructions as described above in connection with proximal portion 20.

Figure 15:
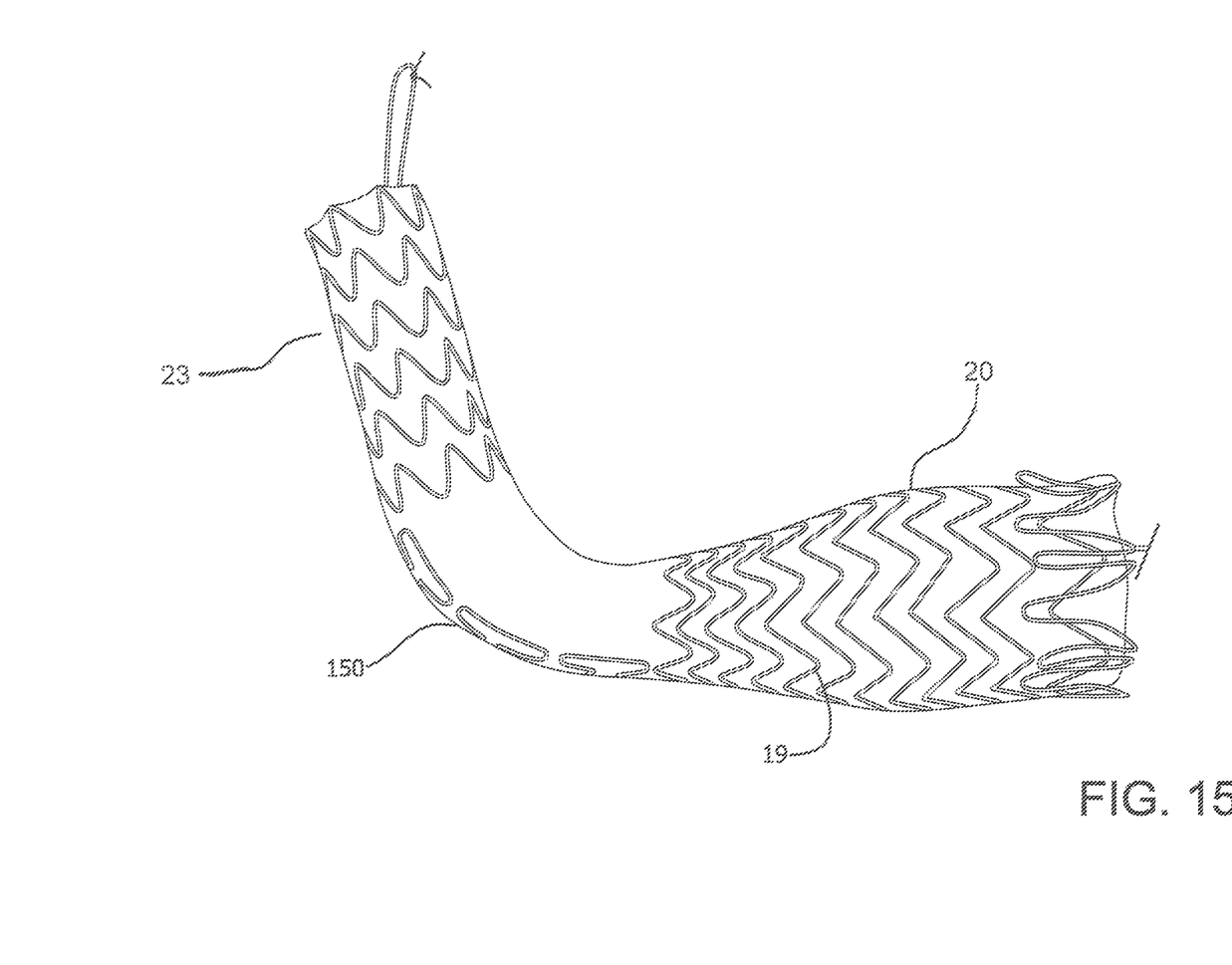
FIG. 15 is a perspective view of another embodiment of the present invention.

FIG. 15 depicts yet another alternative support structure 19 in which portions along the length of the device are unsupported while regions of both the distal portion 23 and the proximal portion 10 are supported.

As shown in FIGS. 2-4, the device also includes a distal portion 13, connected to proximal portion 20. Distal portion 23 may be adapted to extend through abdominal wall 24 to conduct the intestinal contents out of proximal portion 20. At least distal portion 23 may be kink resistant to prevent twisting or kinking thereof. This may be done by constructing distal portion 23 of any biocompatible material that can be made into a tube. Preferably, distal portion 23 is made of ePTFE, reinforced by a support structure similar to that described above in connection with support structure 19. FIG. 4 illustrates a preferred embodiment wherein the support structure for distal portion 23 is a series of nitinol rings. Alternatively, the reinforcement can be FEP. In certain embodiments, the material of the distal portion may comprise at least one aperture therein.

Distal portion 23 optionally has an adjustable length to accommodate different width of abdominal wall 24. The adjustable length may be provided by selection of material that is cut to size, or by use of corrugated or telescoping construction to facilitate compressibility or extension.

Devices of the present invention may further comprise a funnel structure (not shown) at the distal end of the device which could assist in preventing migration or movement of the device and potentially avoid pull through of the device through the stoma.

The device of the present invention optionally includes a transitional portion 25 connecting proximal portion 20 to distal portion 23 for attaching intestine 11 to an inner wall 16 of the abdominal wall 24. A flange or other securing means 18 is optionally also included at the opening to connect and seal distal portion 23 to the patient's skin.

In alternative embodiments, the device of the present invention includes a valve incorporated at any point along the device, preferably the valve could be connected to either the proximal portion 20 or the distal portion 23 for providing continence to the patient, thereby allowing intestinal contents to be selectively discharged from distal portion 23. A valve located in proximal portion 20 may provide an advantage in that the larger diameter of the valve opening could allow for easier passage of material and potentially reduce the risk of blockage. In another embodiment, a valve may be located in a proximal portion 20 of the device but controlled from the distal portion 23.

Figure 5:
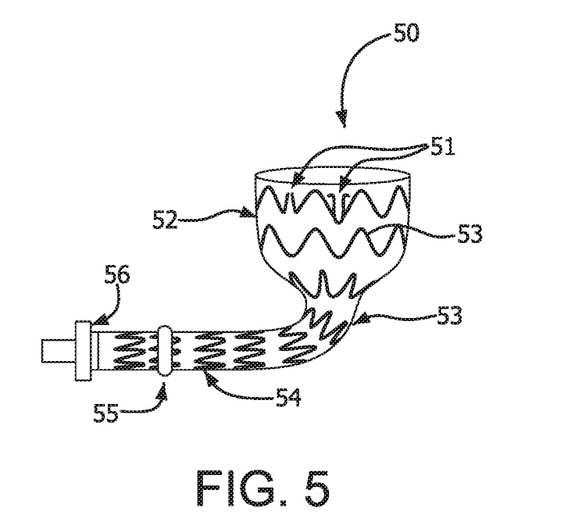
FIG. 5 is a side view of another exemplary embodiment of the present invention.

FIG. 5 depicts an embodiment of the present invention including retention means 51, which can be barbs or scales or the like, on proximal portion 52 for retaining device 50 in place within the intestine. Support structure 53 in this embodiment comprises nitinol stent rings that extend the entire length from proximal portion 52 through and including distal portion 54. In this embodiment, device 50 also includes a retention collar 55 and an iris valve 56 pneumatically actuated. Retention collar 55 is designed to be on the inside wall of the abdomen to prevent movement or migration of device 50 out of the patient. Iris valve 56 is intended to allow a patient to have control over the external release of intestinal contents and is designed to be disposed outside the body.

Figure 6:
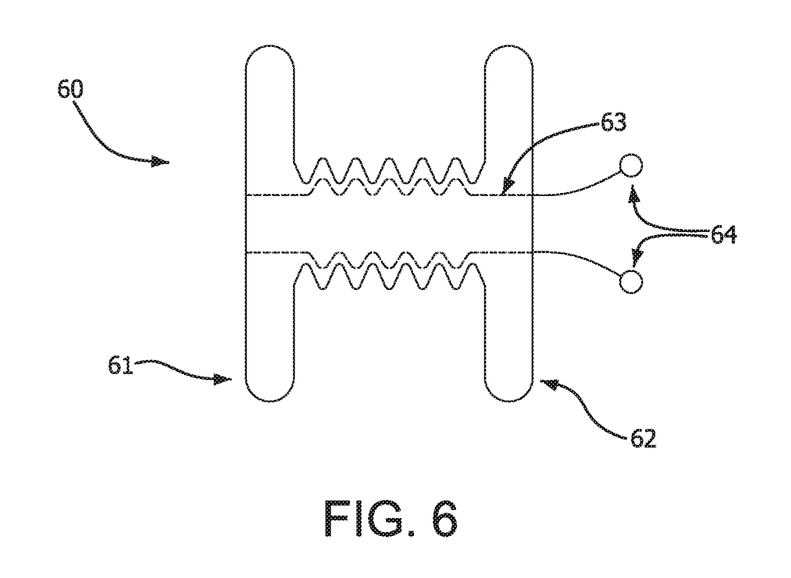
FIG. 6 is a side view of another aspect of the present invention.

FIG. 6 illustrates another aspect of the invention. FIG. 6 shows a dual disc fistula collar 60. Collar 60 is preferably made from a bioresorbable material that is designed to last as long as the device is intended to be in place. A more permanent device may be used, and for example, an ePTFE scaffold can be used with the bioresorbable material. The purpose of fistula collar 60 is to anchor the inside of the intestine to the abdominal wall. This provides support for the device that passes through the middle of collar 60 via lumen 63. This facilitates sealing of the intestine so that intestinal contents do not leak in the abdominal cavity. A retention collar (55, FIG. 5) on device 50 keeps device 50 from being withdrawn into the abdominal cavity. End 61 of collar 60 is designed to be placed inside the intestine, while end 62 is designed to be placed against the abdominal wall. Compression cords 64 are pulled after placement to allow accordion effect of central lumen 63 to clamp down on device 50 and draw the intestine towards the abdominal wall.

Figure 7:
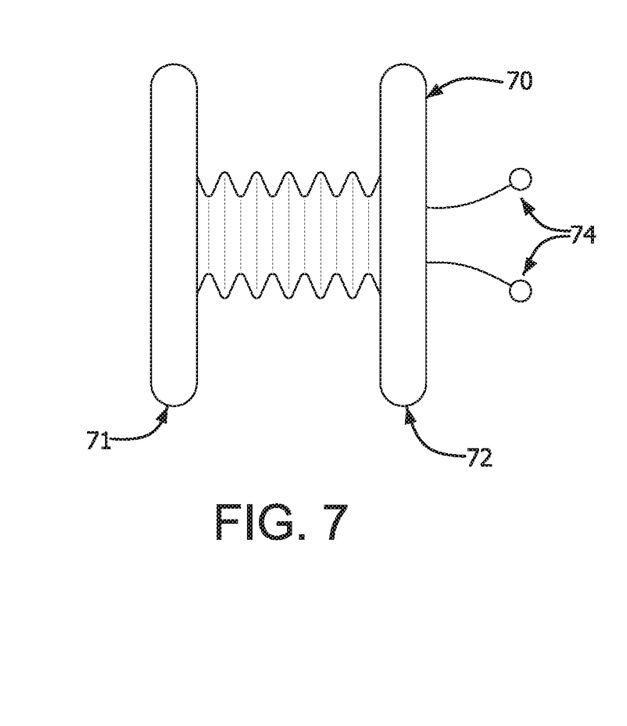
FIG. 7 is a side view of another aspect of the present invention.

Another aspect of the invention is illustrated in FIG. 7. FIG. 7 illustrates an intestinal plug 70 which is used to seal the natural fistula channel that remains after removal of the device. Intestinal plug 70, as with dual disc fistula collar 60, can be made from a bioresorbable material, alone or with a scaffold made, for example, of ePTFE to provide strength and longer life. The dual disc fistula collar 60 is left behind in vivo after removal of the device. The design of intestinal plug 70 is similar to dual disc fistula collar 60 but without the central lumen 63. End 71 of intestinal plug 70 is designed to be placed in the intestine, and end 72 is designed to be placed against the abdominal wall. Compression cords 74 pull the two discs 71 and 72 together.

Figure 8:
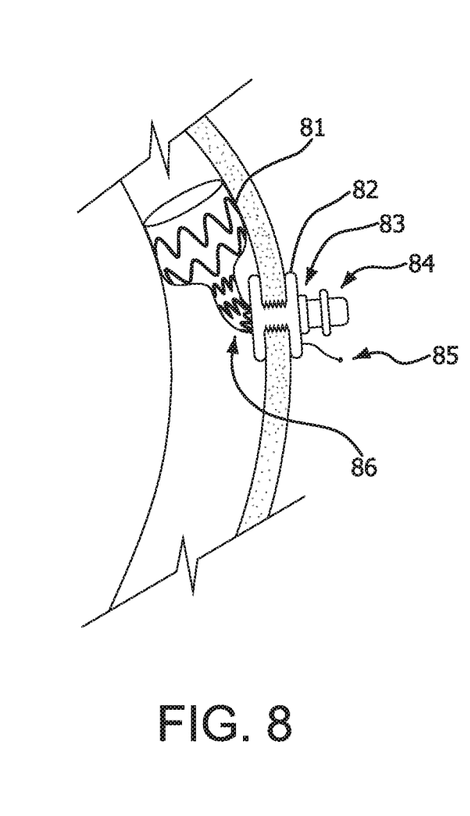
FIG. 8 is a side view of another exemplary embodiment of the present invention.

FIG. 8 illustrates an embodiment of the invention in which the in-dwelling device is shown post-placement and before removal. Proximal portion 81 diverts intestinal contents. Dual disc fistula collar 82 anchors the device in place. Retention collar 83 prevents the device from retracting into the intestine. Iris valve 84 allows patient to control release of intestinal contents. Compression cords 85 seal and pull intestine toward abdominal wall. Support structure 86 in this embodiment is a nitinol frame which comprises a spine that creates a preferential bend in the device that helps hold it in place within the intestine but is flexible enough to allow removal of the device with a removal sheath. Note that the bottom of the device bend is held in place by the dual disc fistula collar 82.

Figure 9:
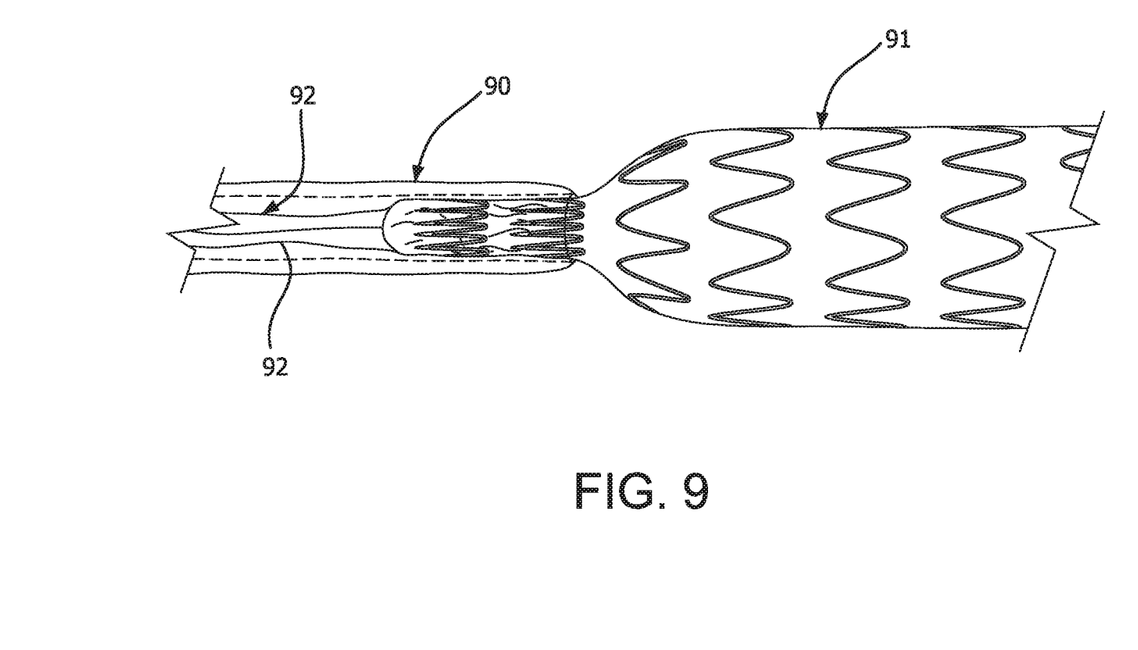
FIG. 9 is a side view of another aspect of the present invention.

FIG. 9 illustrates removal of the device according to the present invention. A removal sheath 90 is used to compress the device so that it can be removed percutaneously, ideally in an outpatient setting. Removal sheath 90 is a hollow polymeric tube sized to allow the withdrawal of the device 91, in the illustrated embodiment, into the central lumen of the removal sheath 90. Removal sheath 90 is rigid enough to prevent collapse or accordioning when removing device 91. Tensioning members 92 are attached to the end of device 91 (after removal of the valve) to pull the stent graft into the sheath. The sheath is advanced as the tensioning members are pulled to completely capture device 91 then removed from the patient. FIG. 9 is an illustration of device 91 in the process of being retracted into sheath 90.

Figure 10:
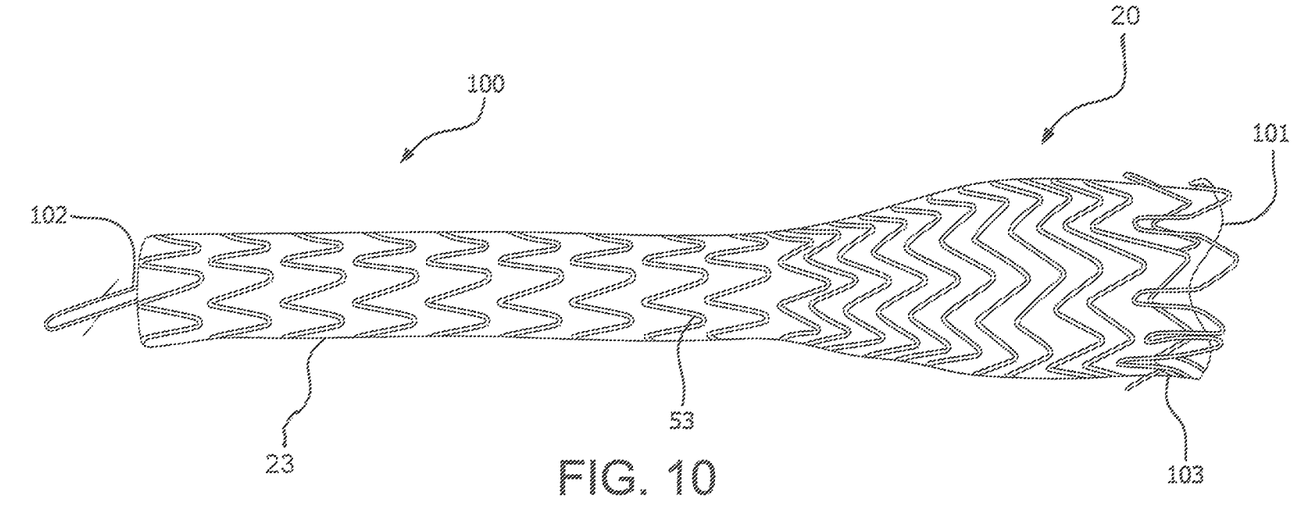
FIG. 10 is a side view of another embodiment of the present invention.
Figure 11:
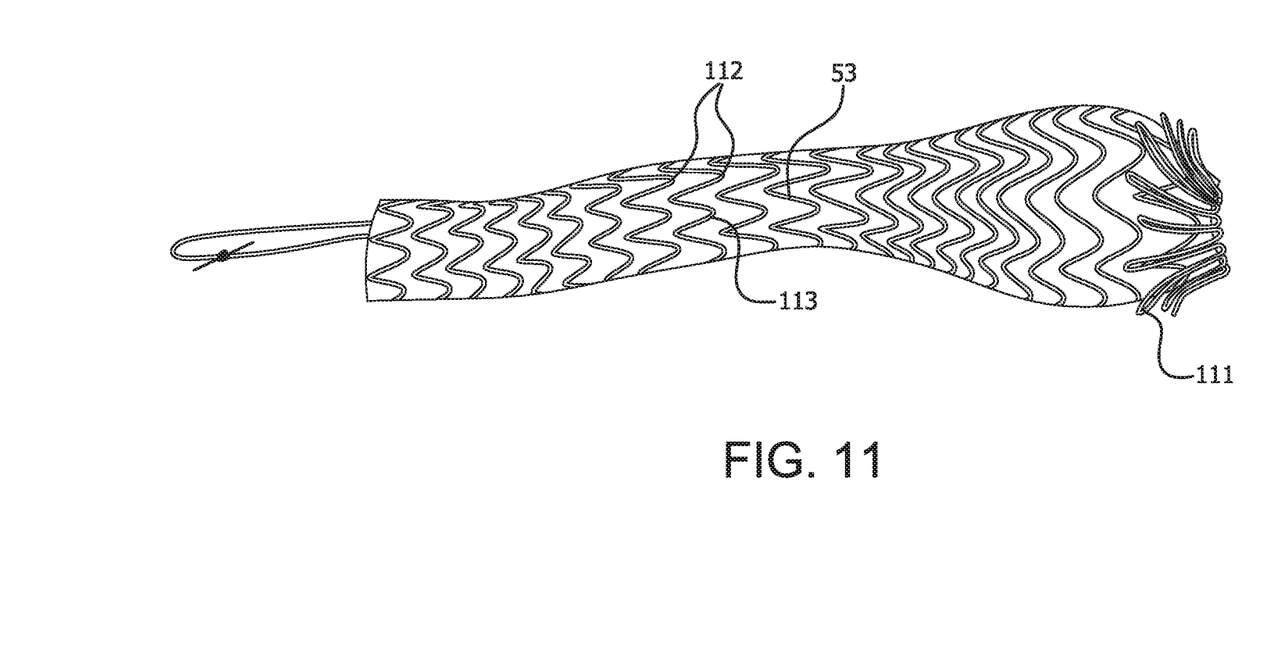
FIG. 11 is a side view of the embodiment of FIG. 10 commencing inversion.
Figure 12:
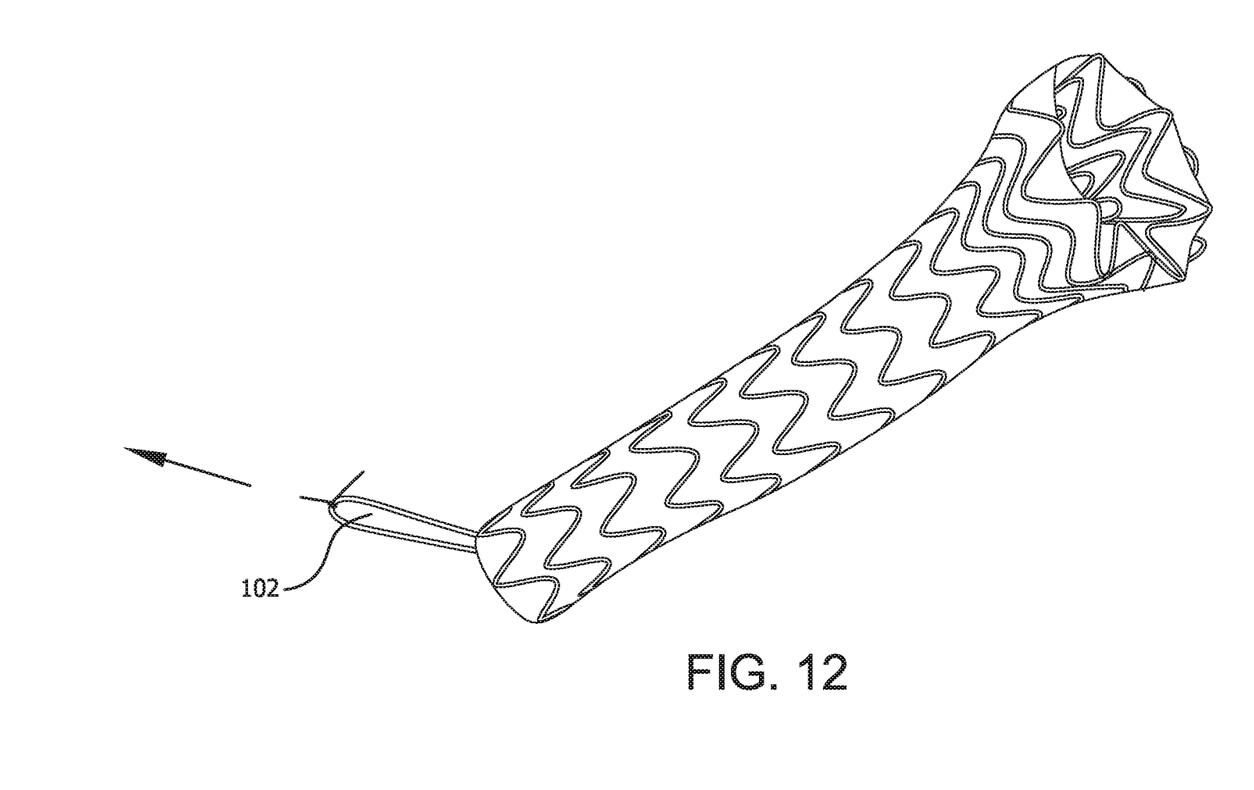
FIG. 12 is a perspective view of the embodiment of FIG. 10 partially inverted.

An alternative method of removal is demonstrated in FIGS. 10-12 wherein the proximal end of the device can be inverted into the main channel of the device for ease of removal. FIG. 10 shows an embodiment of the present invention comprising a radial component 101 that reduces the diameter of the proximal portion 20, or at least the proximal end 103 of the device 100. In communication with the radial component 101 is a tensioning member 102, which may be in the form of, for example, a tensioning cord or retrieval line. The tensioning cord or retrieval line may be a separate member from the radial component or may be an extended end portion of the radial component. Upon force being applied to the tensioning member, as in FIG. 11, tension is applied to the radial component 101 which reduces the diameter of at least the proximal end of the device and anchor fins 111, positioned circumferentially on the proximal portion and/or proximal end of the device are disengaged from the surrounding tissues. Once the proximal end is so reduced, additional force applied to the tensioning member 102 serves to pull the proximal end of the device into a main channel of the device and begin the inversion process as shown in FIG. 12. The larger diameter of the proximal portion is thereby reduced.

In yet another embodiment, the device of the present invention can be pulled apart in a controlled manner in order to ease removal from the intestine or other hollow body cavity or organ. In one embodiment, to facilitate the pull apart method the device may comprise a retrieval line that is attached directly to the proximal end of the support frame, such as a nitinol, one piece, wire frame. Pulling on the retrieval line would pull the proximal end of the support out of the graft material. Continued tension on the retrieval line would continue to pull the nitinol wire free of the graft material in a continuous length. In one embodiment, when enough of the wire has been pulled out that the supported proximal region has a diameter similar to that of the stoma, the device can be removed. Alternatively, where a device comprises a one piece nitinol wire support frame but no retrieval line is present, one could begin pulling on the distal end of the nitinol wire. This method would require the user to unravel most of the device prior to removal as the largest diameter portion of the device would be unraveled last.

Figure 13:
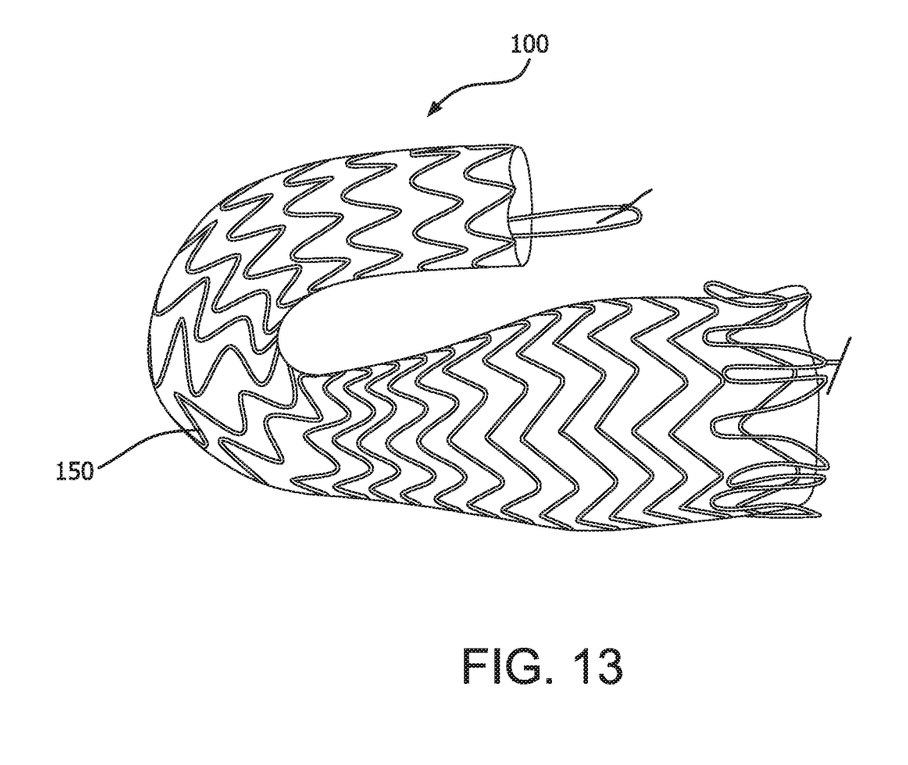
FIG. 13 is a side view of one embodiment of the device of the present invention preferentially bent into a C-shape orientation.

As described above, the devices of the present invention may further comprise a preferential bending mechanism which imparts a radius of curvature to a region of the device, preferentially in one direction, upon expansion of the device. The region of the device capable of achieving a radius of curvature may be located in the proximal portion of the device, the distal portion of the device or any transitional portion therebetween. The preferential bending mechanism may be in the form of a spine along one side of a region of the device. Where the device comprises a support frame, an asymmetrical support frame on opposing sides could provide a suitable spine to achieve preferential bending of the device upon expansion. As shown in FIG. 11, where the device comprises a support frame 53, longer apical distances 112 between apices 113 on adjacent stent rings along at least a region of one side of the device could provide a spine for the device and would be a suitable preferential bending mechanism. Alternatively, the preferential bending mechanism may be in the form of bridging members along a length of device connecting adjacent stent rings on one side of the device thereby creating a spine. Alternatively, a spine could comprise an area of denser barrier material along one side of a region of the device or any other longitudinal stiffening member. FIG. 13 shows the device preferentially bent along the spine 150 of the device 100 in order to render the device into a c-shape or j-shape. In FIG. 15 the spine 150 of the device comprises a longitudinal support structure along one side of an otherwise unsupported region of the device which provides a suitable preferential bending mechanism.

Figure 14:
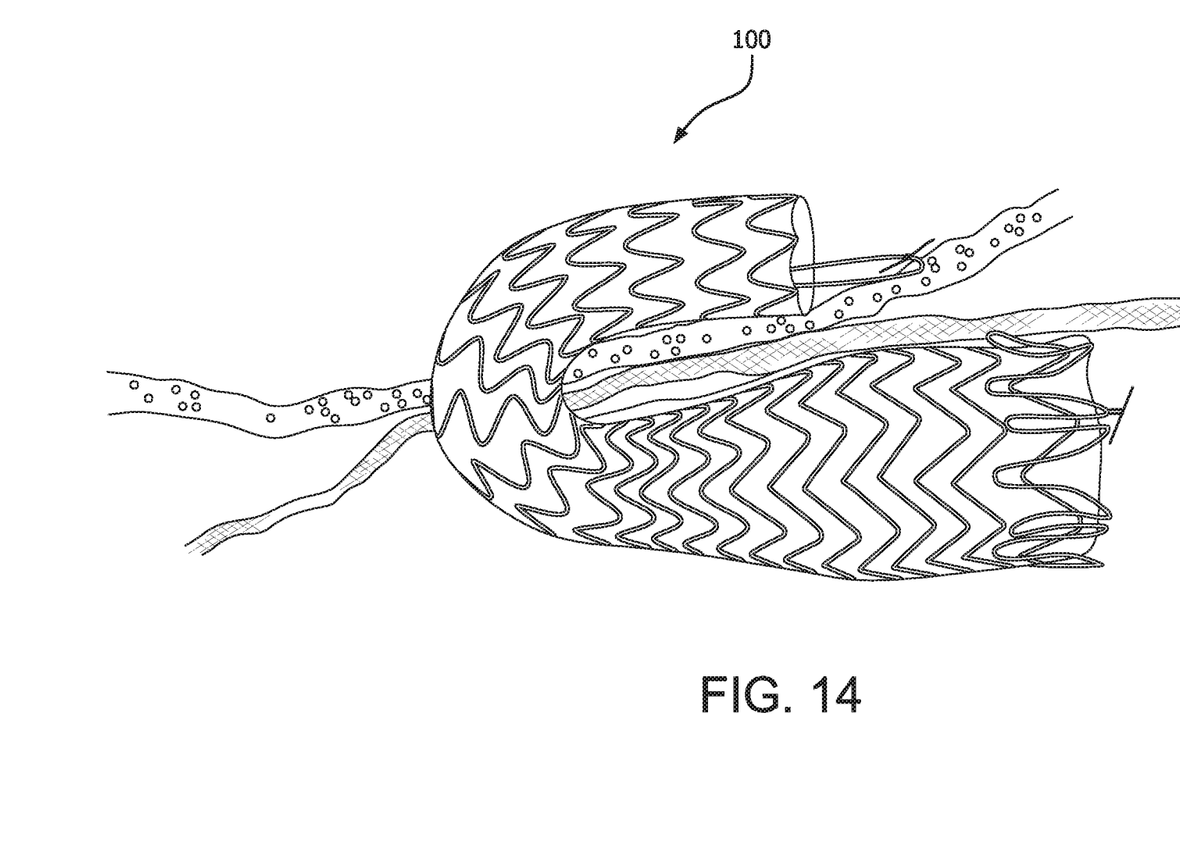
FIG. 14 is a perspective view of the device of FIG. 13 in use.

The preferential bending mechanism may further comprise a locking feature that allows the device to remain in the bent position, until such time as the lock is removed or opened. One advantage to locking the device into a preferentially bent orientation is that the device itself can operate as a clamp, thereby clamping surrounding tissues and eliminating the need for supplemental anchoring component to keep the anchor in place and prevent migration. Generally, the proximal portion of the device would be located within a first hollow body cavity or organ and the distal end of the device could be located in a second hollow body cavity, suitable for receiving drainage from the first, or, alternatively, through the abdominal wall. However, the devices of the present invention may further be held in place by adherence to the surrounding tissue, for example, by suturing or other means. FIG. 14 shows a locked and preferentially bent device 100 in use and connecting two hollow body cavities or organs.

Any number of active agents, such as antimicrobials, may also be included as fillers or coatings in conjunction with any of the embodiments described herein.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A medical device comprising:
a first end portion having a first aperture and defining a first diameter and configured to abut a first tissue surface, the first end portion having a first disc shape;
a second end portion having a second aperture and defining a second diameter and configured to abut a second tissue surface, the second end portion having a second disc shape;
a middle portion configured to form a passage between the first and second tissue surfaces, the middle portion defining a lumen that extends from the first aperture of the first end portion to the second aperture of the second end portion, the middle portion being situated between the first and second end portions and having a third diameter that is less than both the first and second diameters, the middle portion being adjustable from a first length to a second length to compress the first end portion toward the second end portion; and
a cord operable to impart a compression force on the middle portion to compress the first end portion toward the second end portion to facilitate deployment.

2. The medical device of claim 1, wherein the middle portion is adjustable from the first length to the second length such that the third diameter is reduced.

3. The medical device of claim 1, wherein the cord is operable to be tensioned to compress the first end portion toward the second end portion.

4. The medical device of claim 1, wherein the middle portion is configured to adopt an accordion shape when adjusted from the first length to the second length.

5. The medical device of claim 1, wherein the middle portion is configured to be expanded and compressed to adjust the length of the middle portion.

6. The medical device of claim 1, wherein the first and second end portions and the middle portion comprise a polymer.

7. The medical device of claim 6, wherein the first and second end portions and the middle portion comprise ePTFE.

8. The medical device of claim 1, wherein the first and second end portions and the middle portion are bioresorbable.

9. The medical device of claim 1, wherein the first and second end portions are disc-shaped.

10. The medical device of claim 1, wherein the medical device is configured to fluidly couple a plurality of hollow body cavities together.

11. The medical device of claim 1, wherein the medical device is configured to fluidly couple a plurality of organs together.

12. The medical device of claim 11, wherein the plurality of organs is selected from an intestine, a stomach, a gall bladder, a bladder, a pseudocyst, a peritoneal cavity, and a thoracic cavity.

13. The medical device of claim 1, further comprising a valve incorporated in one of the first end portion, the second end portion, and the middle portion.

14. A medical device comprising;
a body having a first a first disc at a first end of the body and a second disc at a second end of the body, the first and second discs being separated by a middle portion of the body that is configured to be adjusted from a first length to a second length; and
a cord configured to transition the body from an expanded state to a contracted state wherein the first and second discs are closer in proximity to one another in the contracted state than in the expanded state.

15. The medical device of claim 14, wherein the body of the medical device comprises a polymer.

16. The medical device of claim 15, wherein the body of the medical device comprises ePTFE.

17. The medical device of claim 14, wherein a lumen extends through the body of the medical device, the lumen being operable to enable a transfer of contents through the body of the medical device.

18. The medical device of claim 17, wherein the two portions are selected from an intestine, a stomach, a gall bladder, a bladder, a pseudocyst, a peritoneal cavity, and a thoracic cavity.

19. The medical device of claim 14, wherein the middle portion is configured to be expanded and compressed to adjust the middle portion between the first and second lengths.

20. The medical device of claim 14, further comprising a valve incorporated in one of the first disc, the second disc, and the middle portion.

21. A method of forming a passage between body structures of a patient, the method including:
    providing a medical device including:
        a first end portion and a second end portion, the first end portion having a first aperture and defining a first diameter and having a first disc shape, the second end portion having a second aperture and defining a second diameter and having a second disc shape, wherein a middle portion couples the first end portion to the second end portion, the middle portion defining a lumen that extends from the first aperture of the first end portion to the second aperture of the second end portion, the middle portion having a third diameter that is less than both the first and second diameters, and the middle portion being adjustable from a first length to a second length; and
        a cord;
    positioning the medical within a body of a patient such that the first apposition portion abuts a first tissue surface, and such that the second apposition portion abut a second tissue surface, and such that the middle portion forms a passage between the first and second tissue surfaces; and
adjusting the middle portion from the first length to the second length by tensioning the cord to compress the first end portion toward the second end portion to facilitate deployment.

* * * * *